United States Patent [19]
Haemmerle et al.

[11] Patent Number: 6,050,979
[45] Date of Patent: Apr. 18, 2000

[54] MEDICAL DEVICE FOR IMPROVING SKIN FIXATION OF INDWELLING CATHETERS AND OTHER TRANSCUTANEOUS IMPLANTS WITH A REDUCED RISK OF INFECTION

[75] Inventors: Hugo Haemmerle, Tuebingen; Fritz Schindler, Gelsenkirchen, both of Germany

[73] Assignee: Huels Aktiengesellschaft, Marl, Germany

[21] Appl. No.: 09/110,126

[22] Filed: Jul. 6, 1998

[51] Int. Cl.[7] .................................................. A61M 5/32
[52] U.S. Cl. ................................. 604/265; 604/175
[58] Field of Search ........................... 604/174, 175, 604/264, 265; 623/1, 11

[56] References Cited

U.S. PATENT DOCUMENTS

| | | |
|---|---|---|
| 4,623,329 | 11/1986 | Drobish et al. . |
| 4,687,471 | 8/1987 | Twardowski et al. . |
| 4,772,269 | 9/1988 | Twardowski et al. . |
| 5,049,140 | 9/1991 | Brenner et al. . |
| 5,057,075 | 10/1991 | Moncrief et al. . |
| 5,098,413 | 3/1992 | Trudell et al. . |
| 5,141,499 | 8/1992 | Zappacosta . |
| 5,308,338 | 5/1994 | Helfrich . |
| 5,723,007 | 3/1998 | Engel et al. .............................. 623/11 |
| 5,800,529 | 9/1998 | Brauker et al. ........................... 623/11 |

*Primary Examiner*—Corrine McDermott
*Attorney, Agent, or Firm*—Oblon, Spivak, McClelland, Maier & Neustadt, P.C.

[57] ABSTRACT

A transcutaneous medical device which has on its surface a fibrous material with free collagen fibers which are present in a natural structure. The transcutaneous medical device is prepared by applying to the surface of such a device a fibrous material with free collagen fibers present in a natural structure.

26 Claims, 2 Drawing Sheets

MEDICAL DEVICE FOR IMPROVING SKIN FIXATION OF INDWELLING CATHETERS AND OTHER TRANSCUTANEOUS IMPLANTS WITH A REDUCED RISK OF INFECTION

BACKGROUND OF THE INVENTION

1. Field of the Invention

The present invention relates to transcutaneous medical devices and to a process for their production.

Transcutaneous medical devices are implants such as, for example, indwelling catheters which pass through the skin and remain in the body for a lengthy period.

2. Description of the Background

Examples of transcutaneous implants include catheters for peritoneal dialysis and catheters for long-term perfusion therapies. However, on long-term use of these and other implants, there is a risk of infection by bacteria or other microorganisms entering the body, which intrusion results from various movements of the body which exert transient tensile and compressive forces on the passages by which the implants pass through the skin. Fissures periodically form at the interface between the passages through the skin and the skin tissue, through which microorganisms can enter and infect the body.

Several proposals for the fixation of transcutaneous implants in the skin have been made in order to prevent infections. For example, transcutaneous devices such as catheters for peritoneal dialysis using cuffs are disclosed in the literature for such a purpose.

Cuffs are hollow cylinders which are a few mm to a few cm long, which surround the catheter. The cuffs are placed on the catheter, singly or multiply, by pulling on or by sticking on an appropriate tape. The task of the cuff is to come into close contact with body tissue by way of its outer surface thereby fixing the catheter and preventing microorganisms from migrating into the body at the catheter/body tissue interface. To achieve this objective, the outside of the cuff consists of Dacron (see U.S. Pat. No. 5,057,075), which is a material regarded as compatible with the body or of a porous material (see U.S. Pat. Nos. 5,308,338 and 5,141,499), into which body cells can grow.

As an additional measure to prevent microbial infections entering the body through the passage through the skin, cuffs are occasionally employed in combination with antiseptic substances. U.S. Pat. No. 5,308,338 discloses a tube which passes inside the catheter and through which antiseptic liquids can be delivered to the cuff material.

U.S. Pat. No. 5,049,140 describes the use of antimicrobial substances in the cuff material.

A number of patents which disclose a fixation and/or prevention of infection in connection with the use of transcutaneous catheters include U.S. Pat. Nos. 5,098,413; 5,057,075; 4,772,269; 4,687,471 and 4,623,329. The patents describe catheters of particular geometric embodiments for individual types of use.

Although the use of cuffs in the prior art can extend the period of use of the catheter, after which the catheter must be changed because of signs of infection, the problems of fixation and prevention of infection when the transcutaneous devices are used over a long period use have not yet been satisfactorily solved. In particular, the ingrowth of body tissue into porous materials does not result in a durable connection which reliably prevents the penetration of infectious organisms into the body. The use of antimicrobial and/or antiseptic substances in this connection is to be regarded as a temporary measure which is susceptible to failure and difficult to implement.

Collagen-containing composite materials are known from a different technical area to be materials which readily form adhesions to the human body (German Patent No. 36 327 316, German Application No. 195 29 036.4). A need continues to exist for a way in which to prevent infection in the use of transcutaneous devices in the human body.

SUMMARY OF THE INVENTION

Accordingly, one object of the present invention is to provide a fixed medical device in or on the body which at the same time prevents infection from entering the body by way of the medical device.

Briefly, this object and other objects of the present invention as hereinafter will become more readily apparent can be attained by a transcutaneous medical device which has on its surface a fibrous material with free collagen fibers, which are present in a natural structure, which material to a high degree prevents microbial infection from entering the body through the point where the transcutaneous medical device passes through the skin.

BRIEF DESCRIPTION OF THE DRAWINGS

Various other objects features and attendant advantages of the present invention will be more fully appreciated as the same becomes better understood from the detailed description when considered in connection with the accompanying drawing in which like reference characters designate like corresponding parts throughout and wherein.

DETAILED DESCRIPTION OF THE PREFERRED EMBODIMENTS

Figure 1:
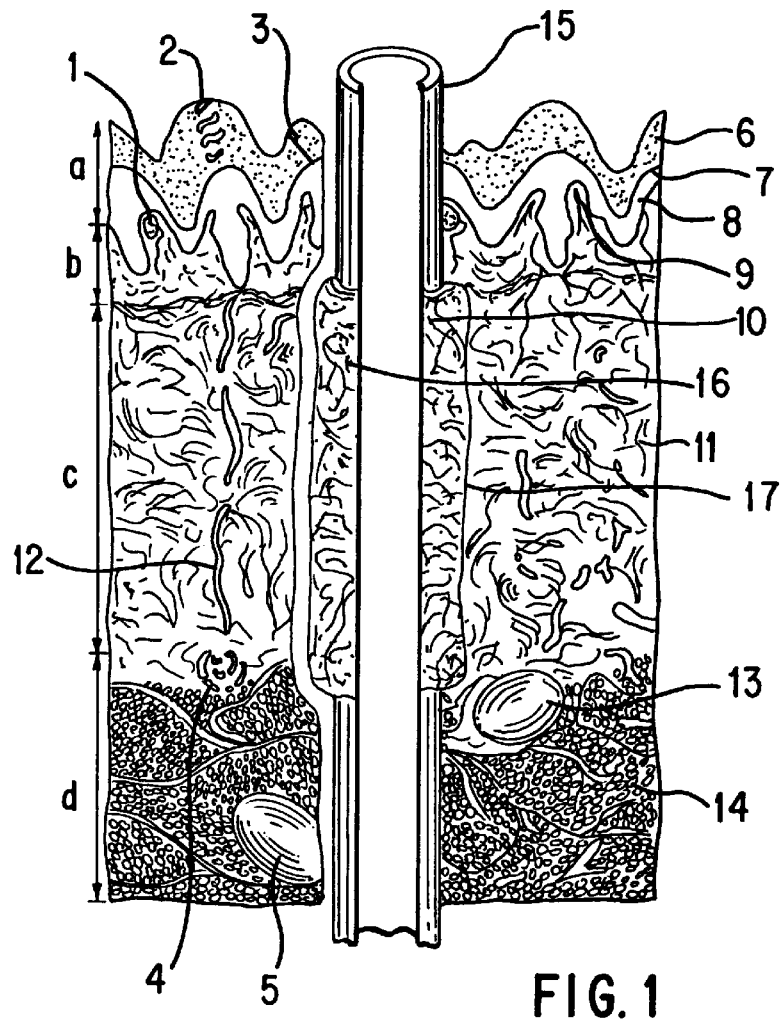
FIG. 1 is a schematic drawing of the transcutaneous medical device of the present invention.
Figure 1A:
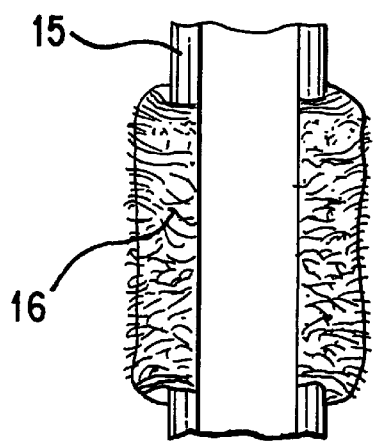

The body tissues adhere, without infection or rejection, to the collagen fibers of the transcutaneous medical device and thus form a durable unit with the transcutaneous medical device. This effective adhesion blocks entry of infectious organisms into the body.

The present transcutaneous medical device has on its surface a fibrous material with free collagen fibers which are present in a natural structure. The present device can be produced by applying a fibrous material with free collagen fibers, which are present in a natural structure.

A preferred embodiment of the transcutaneous medical device of the present invention is prepared by:

(a) preparing a fibrous material by (a1) preparing a collagen felt from collagen fibers which are present in a natural structure, (a2) infiltrating the felt with a polymerizable monomer mixture, (a3) conducting a free-radical polymerization in the presence of polymerization inhibitors which act out from the surface of the infiltrated felt, and (a4) detaching the incompletely polymerized surface layer of the resulting polymer to expose the collagen fibers by treatment of incompletely polymerized material with a suitable solvent and (b) subsequently applying the fibrous material produced in this manner to the surface of a transcutaneous medical device.

A preferred method of preparing the transcutaneous medical device of the invention is conducted by (a) preparing a fibrous material by (a1) preparing a collagen felt from collagen fibers which are present in a natural structure, (a2) infiltrating the felt with a polymerizable monomer mixture, (a3) conducting a free-radical polymerization in the presence of polymerization inhibitors which act out from the surface of the infiltrated felt, and (a4) detachment of the incompletely polymerized surface layer of the resulting polymer to expose the collagen fibers by using suitable solvents and subsequently (b) applying the fibrous material which has been produced to the surface of a transcutaneous medical device.

The fibrous material of the invention is a collagen-containing composite material whose surface forms a felt of free collagen fibers which are present in a natural structure. This collagen/polymer composite material is produced by first obtaining, as disclosed in German Patent Application "Biocompatible Composite Material and Process for its Production" (German Application No. 195 29 036.4), a felt from free collagen fibers which are present in a natural structure, and subsequently infiltrating the fibrous material with a polymerizable monomer preparation. If the monomer preparation contains no polymerization initiators, the polymerization is initiated, for example, by exposure to radiation. The polymerization must in all cases be carried out with surface quenching. This results in a collagen-containing composite material with a incompletely polymerized layer on the surface. This layer is detached with a suitable solvent to expose the collagen fibers. It is possible to influence the thickness and characteristics of the surface layer which is not cured during the polymerization by the choice of quenching parameters.

An embodiment of the present invention is a transcutaneous medical device which is prepared by applying a fibrous material to the surface of a transcutaneous medical device. The fibrous material is prepared by (i) preparing a collagen felt from collagen fibers which are present in a natural structure, (ii) infiltrating the felt with a polymerizable monomer mixture, (iii) applying the felt impregnated to the surface of a transcutaneous medical device, (iv) conducting a free-radical polymerization in the presence of polymerization inhibitors which act out from the surface of the infiltrated felt and (v) detaching of the incompletely polymerized surface layer of the resulting polymer by treatment of felt with a suitable solvent thereby exposing the collagen fibers.

Besides application of the fibrous material to the transcutaneous medical device, this material can also be produced directly on the surface of the transcutaneous medical device. A process of this type is conducted by (i) producing a collagen felt from collagen fibers which are present in a natural structure on the surface of a device, (ii) infiltrating the felt with a polymerizable monomer mixture, (iii) applying the felt impregnated with the monomer mixture to the surface of the transcutaneous medical device, (iv) conducting a free-radical polymerization in the presence of polymerization inhibitors which act out from the surface of the impregnated felt, and (v) detaching the incompletely polymerized surface layer of the resulting polymer by exposing the collagen fibers to a suitable solvent.

The central feature of the present invention is the use of special materials in the production of transcutaneous medical devices. These collagen/polymer composite materials have on their surface free collagen fibers which are present in a natural structure and are presumably responsible for the surprisingly rapid and complete incorporation and adhesion of these materials to body tissues such as, for example, cutaneous connective tissue. Transcutaneous medical devices which comprise these collagen/polymer composite materials at specific points, for example in the form of cuffs, adhere via these materials to the body tissues, which results in fixation of the transcutaneous device on or in the body, and, if these collagen/polymer composite materials are located where the transcutaneous device passes through the body, they impede migration of microbial infectious organisms into the body (see FIG. 1).

FIG. 1 shows the construction of the skin tissue of the human being comprising (a) epithelial layer (epidermus), (b) true skin (corium), which is a layer of connective tissue papillae (stratum papillare), (c) a reticular layer of true skin (stratum reticulare) and (d) subcutaneous fatty tissue. Other features of the skin include Meissner's corpuscle 1, openings of a sweat glad on a ridge 2, free nerve fibers 3, convolutions of the sweat gland 4, lamellated corpuscle in the longitudinal direction 5, cornefied layer (stratum corneum) 6, cornifying layer (stratum granulosum and stratum lucidum) 7, a layer of living epithelial cells (stratum germinativum) 8, capillary loops in the connective tissue papillae 9, cut surface of a small nerve 10, interlaced bundles of connective tissue in the true skin 11, efferent duct of a sweat gland 12, a cross-section through a lamellated corpuscle 13, fatty tissue globules 14, a catheter in section 15, a cuff formed of a collagen/plastic composite material of the invention 16 and a region of adhesion of the skin 17.

Use of a Fine-fiber Collagen

Figure 2:
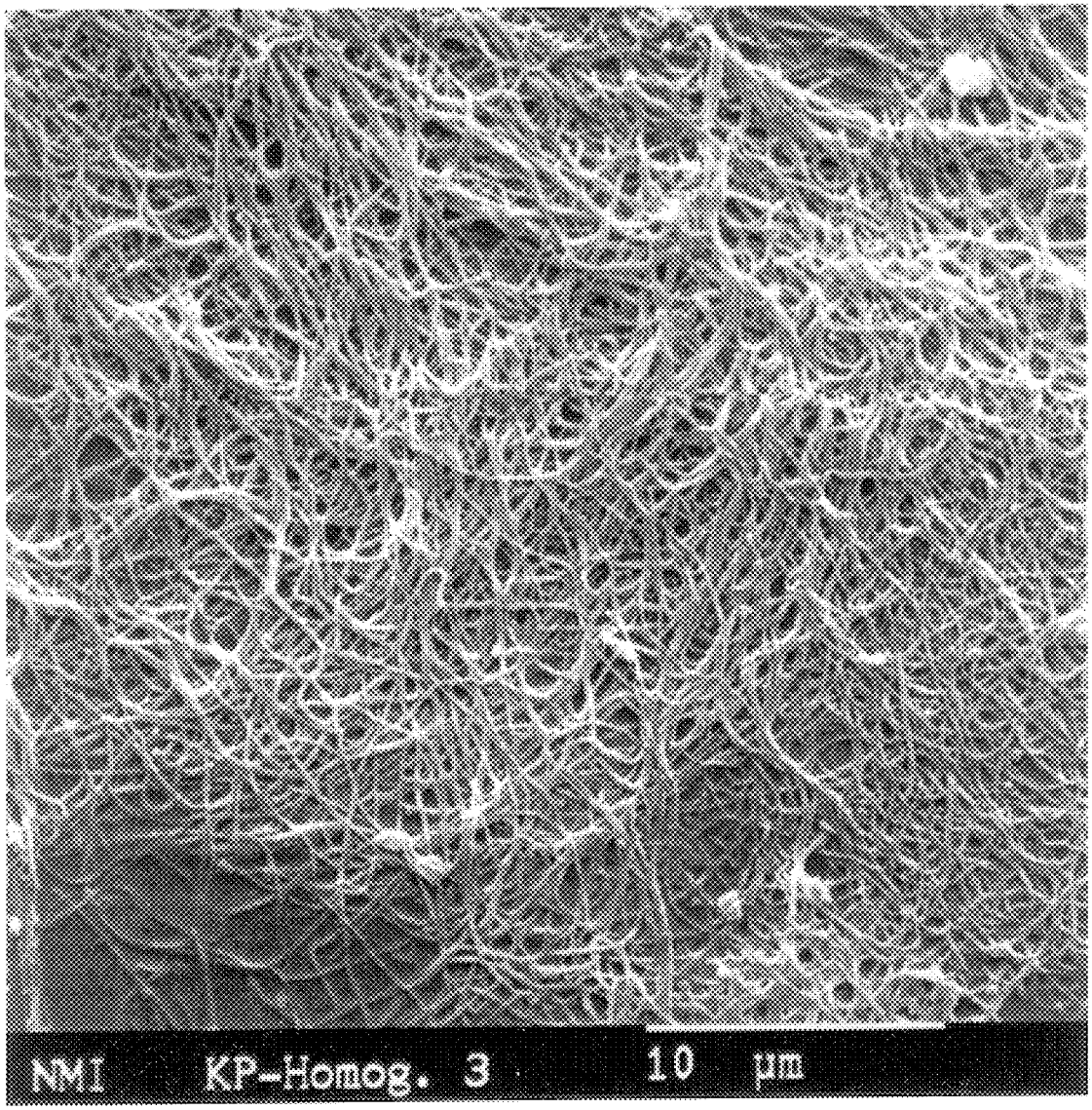
FIG. 2 is a microphotograph showing the final collagen fibers of the transcutaneous medical device of the present invention.

The adhesion property, which the implant material of the invention exhibits, to the skin results from the fine collagen fibers which are anchored in the implant material and project out of the implant surface. These fibers have a diameter of up to 500 nm, preferably of up to about 200 nm, and correspond in their structure to natural collagen (see FIG. 2). The collagen fibers formed by human cells are, therefore, able readily to unite with the collagen fibers of the composite material and ensure favorable incorporation of the transcutaneous medical devices within the body tissue.

Usual commercially available collagen products are more or less denatured, and have lost their native structure.

The following process can be used to produce fine-fiber collagen having a natural structure. Collagen, for example, from bovine or rat tail tendons, is dissolved in dilute acetic acid and then purified by dialysis and centrifugation. The centrifuge supernatant containing the collagen molecules is then removed and transferred into sterile vessels. Adjustment of the pH and of the salt concentration results in the collagen molecules becoming organized in felt-like mats of fine-fiber collagen.

Production of the Collagen/Polymer Composite Materials

A crucial aspect of the successful application of a collagen-containing composite material is the exposure of the native collagen fibers on the surface of the device during its production. This is achieved with the material described herein by impregnation of the collagen mats with curable monomers, for example, methyl methacrylate (MMA), subsequent free-radical polymerization (curing) in the presence of polymerization inhibitors which act out from the surface of the impregnated collagen mats, and then removal of the topmost layer of the collagen/polymer composite material in order to partially expose the collagen fibers (exposed felt).

A process which is based on the principle of inhibition of the polymerization reaction at the surface by oxygen is preferably used. In this process, the collagen mats impregnated with a monomer mixture are polymerized, not in closed molds, but in molds which allow access of oxygen or of an oxygen-containing gas mixture. Since polymerization reactions can be inhibited by oxygen, an uncured outer layer remains on the surface of the samples and is subsequently removed by treatment with a suitable solvent, for example, acetone. It is possible in this manner to expose the collagen fibers on the surface. The thickness of the layer can be controlled by a choice of the appropriate parameters (oxygen concentration, duration of the curing process, light intensity, temperature, solvent, and the like).

It is possible in principle to use, as curable monomers, all substances, singly (homopolymers) or in combination with other monomers (copolymers), which polymerize by a free-radical reaction, such as, for example, styrene, vinyl compounds, maleic anhydride or alkyl acrylates and methacrylates, where the alkyl group may contain 1–12 C atoms. The structure can be linear, branched, cycloaliphatic, aromatic or substituted aromatic. It is furthermore possible to use heterocyclic monomers which have either nitrogen, sulfur or oxygen in the side chain. The monomers can be used as single components or in the form of monomer mixtures or monomer/polymer mixtures with or without fillers.

The polymerizable monomer mixture may contain monomers capable of free-radical polymerization, preferably acrylates, particularly preferably methacrylates.

The polymerizable monomer mixture may furthermore contain one or more compounds selected from the following group: methyl methacrylate, ethyl methacrylate, n-butyl methacrylate, isobutyl methacrylate, 2-ethylhexyl methacrylate, cyclohexyl methacrylate, isobornyl methacrylate, tetrahydrofurfuryl methacrylate, benzyl methacrylate, morpholinoethyl methacrylate, diethylene glycol dimethacrylate, triethylene glycol dimethacrylate, diurethane dimethacrylate (product of the reaction of trim-ethylhexamethylene diisocyanate with two mol of 2-hydroxyethyl methacrylate), isopropylidenebis (2(3)-hydroxy-3(2)-(4-phenoxy)propyl methacrylate) and/or methacrylic acid.

In addition, the polymerizable monomer mixture may contain one or more compounds selected from the following group: styrene, α-methylstyrene, styrenesulfonic acid, vinyl compounds and/or maleic anhydride. Suitable vinyl compounds include ethylene, propylene and butylenes, and also vinyl chloride and butadiene. Other components of the monomer mixture include solvents and/or fillers, and polymerization initiators.

Suitable polymerization initiators which can be used include azonitriles, alkyl peroxides, acylperoxides, hydroperoxides, peroxoketones, peresters and peroxocarbonates, peroxodisulfate, persulfate and all the usual photoinitiators.

The polymerization reaction can likewise be initiated thermally or by exposure of the monomer bearing material to electromagnetic radiation such as, for example, UV-light or γ radiation.

To produce a nonpolymerized layer on the surface of the collagen composite material, the polymerization is carried out in the presence of oxygen or of an oxygen-containing gas mixture. The not completely polymerized layer produced in this manner is then detached by treatment of the composite material with a suitable solvent such as, for example, acetone, methyl ethyl ketone, acetonitrile or THF.

There are several ways in which the material of the invention can be applied to a surface of a transcutaneous medical device such that it has free collagen fibers projecting from the surface:

(i) The still plastic material, which is a mixture of monomers and collagen, is applied to the surface of a medical device. The material is subsequently surface-quenched cured and then the incompletely polymerized material is detached from a surface to prepare the transcutaneous medical device.

(ii) Hollow cylinders are produced by infiltrating a collagen felt with monomer in the wall space of a mold. The highly viscous monomer/collagen material is then removed from the mold, impaled on a spike and polymerized with surface quenching in oxygen or an oxygen-containing gas mixture. After detachment of the incompletely polymerized outer layer with a solvent, hollow cylinders of the polymer/collagen composite material with a smooth inside and an outside with free collagen fibers are prepared. Hollow cylinders with various dimensions can be produced by choice of different molds. The molds preferably used have:

(a) a length of from 0.2–7 cm,
(b) an external diameter of from 0.5–2 cm,
(c) an internal diameter of from 0.2–1.5 cm.

Hollow cylinders which have free collagen fibers on the outside and which have been produced as described above or by another way can be employed in various embodiments for the fixation of transcutaneous implants, for example as:

(i) a cuff which is drawn over the catheter and fixed at the required point by annular tension forces, by the use of a biocompatible adhesive such as, for example, histoacrylic adhesive or by some other ways, (ii) a sheath which is fitted via socket connectors into the catheter, (iii) a sheath which is fixed vertically in the skin and which is left for some weeks therein over which time the sheath is incorporated into the cutaneous tissue. Then a catheter is pushed through the sheath, and the annular gap between the catheter and the inner wall of the sheath is sealed with silicone oil or another suitable material.

In order to assist the tissue incorporation process when employing the collagen/polymer composite materials for transcutaneous medical devices of the invention, the surface of the transcutaneous device can be coated, shortly before its use, with a gel which may contain antibiotics, substances promoting tissue growth and/or other active substances. In order to prepare this gel, an aqueous solution or suspension of the active substances is prepared and is then solidified by adding gel-forming substances.

Constituents of the Gel

Antibiotics:

Antibiotics are employed in gel formation in an amount which, taking account of diffusion losses, prevents sepsis for several days. Particularly suitable antibiotics are penicillin, streptomycin and other, mainly lipophilic antibiotics.

Growth factors:

Adequate amounts of a commercially available epidermal growth factor or other factors such as, for example, fibroblast growth factor or platelet derived growth factor are added. It may be advantageous to add dextran or calcium phosphate together with the growth factors in order to achieve a release slowing effect (European Patent No. 0 530 458, Japanese Patent No. 63-105765).

Formation of the gel:

The aqueous solution or suspension containing the active substances can be converted into a gel in several ways:

(1) by addition of fibrinogen, thrombin and aprotinin,
(2) by addition of collagen as disclosed by Parson-Wingerter and Saltzman (Biotechnol. Prog. 9, pages 600–607/1993),
(3) by addition of a mixture of collagen and calcium phosphate,
(4) by addition of sodium alginate and subsequent initiation of gel formation by addition of $CaCl_2$.

Having now generally described the invention, a further understanding can be obtained by reference to certain specific examples which are provided herein for purpose of illustration only and are not intended to be limiting unless otherwise specified.

Eighteen cylindrical specimens (diameter: 4 mm, length: 15 mm) were implanted dorsally in two rows subcutaneously from cranial to caudal in 3 young male rats. These 18 specimens consisted of:

(1) 3×poly(methyl methacrylate) (PMMA), (2) 6×PMMA/collagen composite material, collagen fibers not crosslinked, (3) 6×PMMA/collagen composite material, collagen fibers crosslinked with glutaraldehyde, (4) 3×polytetrafluoroethylene.

The collagen-containing specimens were produced as follows:

Collagen having a natural structure was infiltrated with a methyl methacrylate monomer mixture (see German Application 195 29 036.4) and then cured in a bowl-shaped curing mold under a halogen lamp emitting light of wavelength maximum at 340 nm for 10 min. Curing was carried out in a desiccator which had previously been flushed with oxygen. The samples were then immersed with agitation in acetone for 10 min to detach the uncured surface layer. In order to produce specimens with crosslinked collagen, the collagen having a natural structure was fixed with glutaraldehyde before infiltration with the monomer mixture.

Since the oxygen had access only to that part of the sample surface which was on top in the bowl-shaped curing mold during the curing step, in the subsequent acetone treatment, free collagen fibers were exposed only on this part of the surface (almost 50% of the total surface).

All the specimens were incorporated without rejection and inflammation into the cutaneous tissue. However, the determination of the tensile forces necessary to extract the implants from the cutaneous tissue of the sacrificed rats, which was carried out after 28 days, showed marked differences:

| Material | Average tensile force used to extract the specimens [N] |
| --- | --- |
| Polytetrafluoroethylene | <1.0 |
| PMMA | 3.0 |
| PMMA/collagen composite material, not crosslinked | 6.5 |
| PMMA/collagen composite material, crosslinked | 5.7 |

The forces required to extract the specimens in the case of the collagen-containing composite materials show the good union of the specimens with the body tissue, especially since the free collagen fibers are exposed only on almost 50% of the total surface of the specimens.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by letters patent is:

1. A transcutaneous medical device which has on its surface a fibrous material having free collagen fibers which are present in a natural structure.

2. A transcutaneous medical device as claimed in claim 1, prepared by:

(a) preparing said fibrous material by:
  (a1) preparing a collagen felt from collagen fibers which are present in a natural structure;
  (a2) infiltrating the collagen felt with a polymerizable monomer mixture;
  (a3) conducting a free-radical polymerization of the monomers in the presence of polymerization inhibitors which act out from the surface of the infiltrated felt;
  (a4) detaching of the incompletely polymerized surface layer of the resulting polymer to expose the collagen fibers by treatment with a solvent; and (b) subsequently applying the fibrous material produced to the surface of a transcutaneous medical device.

3. The transcutaneous medical device as claimed in claim 2, wherein the polymerizable monomer mixture comprises free-radically polymerizable monomers.

4. The transcutaneous medical device as claimed in claim 3, wherein the polymerizable monomer mixture comprises acrylates.

5. The transcutaneous medical device as claimed in claim 3, wherein the polymerizable monomer mixture comprises methacrylates.

6. The transcutaneous medical device as claimed in claim 5, wherein the polymerizable monomer mixture comprises at least one compound selected from the group consisting of:
methyl methacrylate, ethyl methacrylate, n-butyl methacrylate, isobutyl methacrylate, 2-ethylhexyl methacrylate, cyclohexyl methacrylate, isobornyl methacrylate, tetrahydrofurfuryl methacrylate, benzyl methacrylate, morpholinoethyl methacrylate, diethylene glycol dimethacrylate, triethylene glycol dimethacrylate, diurethane dimethacrylate, isopropylidenebis(2(3 )-hydroxy-3(2 )-(4-phenoxy) propyl methacrylate) and methacrylic acid.

7. The transcutaneous medical device as claimed in claim 5, wherein the polymerizable monomer mixture comprises at least one compound selected from the group consisting of:
styrene, α-methylstyrene, styrenesulfonic acid, vinyl compounds and maleic anhydride.

8. A transcutaneous medical device as claimed in claim 1, prepared by:

preparing a collagen felt from collagen fibers which are present in a natural structure;

infiltrating the felt with a polymerizable monomer mixture;

applying the infiltrated felt to the surface of the transcutaneous medical device;

conducting a free-radical polymerization of the monomers in the presence of polymerization inhibitors which act out from the surface of the infiltrated felt; and detaching the incompletely polymerized surface layer of the resulting polymer to expose the collagen fibers by treatment with a solvent.

9. The transcutaneous medical device as claimed in claim 8, wherein the polymerizable monomer mixture comprises free-radically polymerizable monomers.

10. The transcutaneous medical device as claimed in claim 9, wherein the polymerizable monomer mixture comprises acrylates.

11. The transcutaneous medical device as claimed in claim 9, wherein the polymerizable monomer mixture comprises methacrylates.

12. The transcutaneous medical device as claimed in claim 11, wherein the polymerizable monomer mixture comprises at least one compound selected from the group consisting of:

methyl methacrylate, ethyl methacrylate, n-butyl methacrylate, isobutyl methacrylate, 2-ethylhexyl methacrylate, cyclohexyl methacrylate, isobornyl methacrylate, tetrahydrofurfuryl methacrylate, benzyl methacrylate, morpholinoethyl methacrylate, diethylene glycol dimethacrylate, triethylene glycol dimethacrylate, diurethane dimethacrylate, isopropylidenebis(2(3)-hydroxy-3(2)-(4-phenoxy) propyl methacrylate) and methacrylic acid.

13. The transcutaneous medical device as claimed in claim 11, wherein the polymerizable monomer mixture comprises at least one compound selected from the group consisting of:

styrene, α-methylstyrene, styrenesulfonic acid, vinyl compounds and maleic anhydride.

14. A process of forming a fibrous collagen material on the surface of a transcutaneous medical device, which comprises:

applying to the surface of a transcutaneous medical device a fibrous material having free collagen fibers which are present in a natural structure.

15. The process as claimed in claim 14, wherein the device is produced by:

(a) preparing said fibrous material by:
(a1) preparing a collagen felt from collagen fibers which are present in a natural structure,
(a2) infiltrating of the felt with a polymerizable monomer mixture,
(a3) free-radically polymerizing the monomer mixture in the presence of polymerization inhibitors which act out from the surface of the infiltrated felt,
(a4) detaching the incompletely polymerized surface layer of the resulting polymer to expose the collagen fibers by treatment with a solvent, and subsequently (b) applying the detached material to the surface of a transcutaneous medical device.

16. The process as claimed in claim 15, wherein the polymerizable monomer mixture comprises free-radically polymerizable monomers.

17. The process as claimed in claim 16, wherein the polymerizable monomer mixture comprises acrylates.

18. The process as claimed in claim 16, wherein the polymerizable monomer mixture comprises methacrylates.

19. The process as claimed in claim 16, wherein the polymerizable monomer mixture comprises at least one compound selected from the group consisting of:

methylmethacrylate, ethyl methacrylate, n-butyl methacrylate, isobutyl methacrylate, 2-ethylhexyl methacrylate, cyclohexyl methacrylate, isobornyl methacrylate, tetrahydrofurfuryl methacrylate, benzyl methacrylate, morpholinoethyl methacrylate, diethylene glycol dimethacrylate, triethylene glycol dimethacrylate, diurethane dimethacrylate, isopropylidenebis(2(3)-hydroxy-3(2)-(4-phenoxy) propyl methacrylate) and methacrylic acid.

20. The process as claimed in claim 16, wherein the polymerizable monomer mixture comprises at least one compound selected from the group consisting of:

styrene, α-methylstyrene, styrenesulfonic acid, vinyl compounds and maleic anhydride.

21. The process as claimed in claim 14, wherein the fibrous material is applied to the surface of a transcutaneous medical device by:

preparing a collagen felt from collagen fibers which are present in a natural structure, infiltrating the felt with a polymerizable monomer mixture, applying the infiltrated felt to the surface of a transcutaneous medical device, free-radically polymerizing said monomer mixture in the presence of polymerization inhibitors which act out from the surface of the infiltrated felt, and detaching the incompletely polymerized surface layer of the resulting polymer to expose the collagen fibers by treatment with a solvent.

22. The process as claimed in claim 21, wherein the polymerizable monomer mixture comprises free-radically polymerizable monomers.

23. The process as claimed in claim 22, wherein the polymerizable monomer mixture comprises acrylates.

24. The process as claimed in claim 22, wherein the polymerizable monomer mixture comprises methacrylates.

25. The process as claimed in claim 22, wherein the polymerizable monomer mixture comprises at least one compound selected from the group consisting of:

methylmethacrylate, ethyl methacrylate, n-butyl methacrylate, isobutyl methacrylate, 2-ethylhexyl methacrylate, cyclohexyl methacrylate, isobornyl methacrylate, tetrahydrofurfuryl methacrylate, benzyl methacrylate, morpholinoethyl methacrylate, diethylene glycol dimethacrylate, triethylene glycol dimethacrylate, diurethane dimethacrylate, isopropylidenebis(2(3)-hydroxy-3(2)-(4-phenoxy) propyl methacrylate) and methacrylic acid.

26. The process as claimed in claim 22, wherein the polymerizable monomer mixture comprises at least one compound selected from the group consisting of:

styrene, α-methylstyrene, styrenesulfonic acid, vinyl compounds and maleic anhydride.

* * * * *

UNITED STATES PATENT AND TRADEMARK OFFICE
CERTIFICATE OF CORRECTION

PATENT NO.   : 6,050,979
DATED        : April 18, 2000
INVENTOR(S)  : Hugo Haemmerle, et al.

It is certified that error appears in the above-indentified patent and that said Letters Patent is hereby corrected as shown below:

On the title page, item [30], the Foreign Application Priority Data has been omitted. It should read as follows:

--[30]   Foreign Application Priority Data

July 3, 1997   [DE]   Germany ...........197 28 489--

Signed and Sealed this

Tenth Day of April, 2001

Attest:

NICHOLAS P. GODICI

Attesting Officer         Acting Director of the United States Patent and Trademark Office